United States Patent
Zahalsky

(10) Patent No.: US 10,751,374 B2
(45) Date of Patent: *Aug. 25, 2020

(54) METHODS AND COMPOSITIONS FOR TREATMENT OF PENILE DEFECTS

(71) Applicant: Michael P. Zahalsky, Parkland, FL (US)

(72) Inventor: Michael P. Zahalsky, Parkland, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/363,142

(22) PCT Filed: Jan. 30, 2013

(86) PCT No.: PCT/US2013/023830
§ 371 (c)(1),
(2) Date: Jun. 5, 2014

(87) PCT Pub. No.: WO2013/116327
PCT Pub. Date: Aug. 8, 2013

(65) Prior Publication Data
US 2015/0164961 A1 Jun. 18, 2015

Related U.S. Application Data

(60) Provisional application No. 61/592,108, filed on Jan. 30, 2012.

(51) Int. Cl.
| | | |
|---|---|---|
| *A61K 35/35* | (2015.01) | |
| *A61K 35/28* | (2015.01) | |
| *C12N 5/0775* | (2010.01) | |
| *A61K 9/00* | (2006.01) | |
| *A61K 35/50* | (2015.01) | |
| *A61K 35/545* | (2015.01) | |
| *A61K 45/06* | (2006.01) | |
| *A61L 27/22* | (2006.01) | |
| *A61L 27/24* | (2006.01) | |
| *A61L 27/36* | (2006.01) | |
| *A61L 27/38* | (2006.01) | |
| *A61L 27/54* | (2006.01) | |
| *A61K 38/18* | (2006.01) | |
| *A61K 47/42* | (2017.01) | |

(52) U.S. Cl.
CPC ............ *A61K 35/35* (2013.01); *A61K 9/0019* (2013.01); *A61K 9/0034* (2013.01); *A61K 35/28* (2013.01); *A61K 35/50* (2013.01); *A61K 35/545* (2013.01); *A61K 38/18* (2013.01); *A61K 45/06* (2013.01); *A61K 47/42* (2013.01); *A61L 27/225* (2013.01); *A61L 27/24* (2013.01); *A61L 27/3633* (2013.01); *A61L 27/3834* (2013.01); *A61L 27/54* (2013.01); *C12N 5/0667* (2013.01)

(58) Field of Classification Search
CPC .... A61K 35/28; A61K 9/0019; C12N 5/0663; C12N 5/0662; A61L 27/3834; A61L 27/3633; A61F 2005/411; G01N 33/5073; A61M 2210/167
See application file for complete search history.

(56) References Cited

U.S. PATENT DOCUMENTS

| | | | |
|---|---|---|---|
| 7,501,115 B2 | 3/2009 | Fraser et al. | |
| 7,687,059 B2 | 3/2010 | Fraser et al. | |
| 2007/0042930 A1* | 2/2007 | Ross et al. | 510/446 |
| 2009/0311223 A1* | 12/2009 | Ichim | A61K 35/28 |
| | | | 424/93.7 |
| 2011/0218396 A1 | 9/2011 | Williams et al. | |
| 2012/0183519 A1 | 7/2012 | Swift | |

FOREIGN PATENT DOCUMENTS

| | | | |
|---|---|---|---|
| WO | 2009120879 A1 | 10/2009 | |
| WO | WO2009120879 | * 10/2009 | ............... C12N 5/08 |
| WO | 2011109026 A1 | 9/2011 | |
| WO | 2013116327 | 8/2013 | |

OTHER PUBLICATIONS

Hellstrom WG. Medical management of Peyronie's disease. J Androl. 2009;30:397-405.*
Xiaflex. Medical management of Peyronie's disease. New York. 2010;1-5.*
Alexander et al., Separating Stem Cells by Flow Cytometry: Reducing Variability for Solid Tissues, Cell Stem Cell, (2009), pp. 579-583 and suppl. mater, vol. 5.
Cytori Therapeutics, Study of Autologous Fat Enhanced with Regenerative Cells Transplanted to Reconstruct Breast Deformities after Lumpectomy (RESTORE-2), Clinical Trial, (2011).
Frantz et al., The Extracellular Matrix at a Glance, J Cell Sci, (2010), pp. 4195-4200, vol. 123, No. 24.
Gimble et al., Adipose-Derived Stem Cells for Regenerative Medicine, Circ. Res., (2007), pp. 1249-1260, vol. 100.
Hauck et al., A Critical Analysis of Nonsurgical Treatment of Peyronie's Disease, Eur. Urol., (2006), pp. 987-997, vol. 49.
Kendirci et al., Transplantation of Non-Hematopoietic Adult Bone Marrow Stem/Progenitor Cells Isolated by the p75 Nerve Growth Factor Receptor into the Penis Rescues Erectile Function in a Rat Model of Cavernous Nerve Injury, J. Urol., (2010), pp. 1560-1566, vol. 184, No. 4.

(Continued)

*Primary Examiner* — Lynn Y Fan
(74) *Attorney, Agent, or Firm* — David L. King

(57) ABSTRACT

A composition for use in treating penile defects, including erectile dysfunction and Peyronie's disease, is provided. The composition includes adipose tissue and stem cells. The stem cells may be derived from adipose tissue. In embodiments the composition includes additional additives such as growth factors, anti-inflammatories, antioxidants, compositions useful for wound healing, and collagenases. Also provided is a method of treating a penile defect in a patient. The method includes providing a composition containing adipose tissue and stem cells, and implanting that composition into a patient in need of treatment for a penile defect. In some embodiments the patient has Peyronie's disease. In other embodiments, the patient has erectile dysfunction.

7 Claims, No Drawings

(56) References Cited

OTHER PUBLICATIONS

Kondo et al., Implantation of Adipose-Derived Regenerative Cells Enhances Ischemia-Induced Angiogenesis, Arteriosclerosis, Thrombosis, and Vasc. Biol., (2009), pp. 61-66, vol. 29.

Ma et al., Adipose Tissue-Derived Stem Cell-Seeded Small Intestinal Submucosa for Tunica Albuginea Grafting and Reconstruction, PNAS, (2012), pp. 2090-2095, vol. 109, No. 6.

Meyerrose et al., In Vivo Distribution of Human Adipose-Derived Mesenchymal Stem Cells in Novel Xenotransplantation Models, Stem Cells, (2007), pp. 220-227, vol. 25.

Thomas, Stem Cells Repair Damaged Corneas in Mice, HealingWell. com (http://news.healingwell.com/index.php?p=news1&id=625948) (2009).

Turksen Ed., Embryonic Stem Cells: Methods and Protocols, (2002), vol. 185, Humana Press.

Weiler-Mithoff et al., Single Treatment Cell-Enhanced Reconstruction After BCT: a Proven Technique (Early outcomes of RESTORE-2), Thirty-Second Annual CTRC-AACR San Antonio Breast Cancer Symposium, (2009).

Woo et al., Transplantation of Muscle-Derived Stem Cells into the Corpus Cavernosum Restores Erectile Function in a Rat Model of Cavernous Nerve Injury, Korean J Urol, (2011), pp. 359-363, vol. 52.

Zhang et al., Preservation of the Cardiac Function in Infarcted Rat Hearts by the Transplantation of Adipose-Derived Stem Cells with Injectable Fibrin Scaffolds, Exper. Biol. Med., (2010), pp. 1505-1515, vol. 235.

Zhang, et al. "Stem Cells; novel players in the treatment of erectile dysfunction.", Asian Journal of Andrology, (Jan. 2012) vol. 14, No. 1, pp. 145-155, p. 148 col. 2 para2.

* cited by examiner

METHODS AND COMPOSITIONS FOR TREATMENT OF PENILE DEFECTS

CROSS-REFERENCE TO RELATED APPLICATIONS

This application is the United States national phase of International Application No. PCT/US2013/023830 filed Jan. 30, 2013 and claims priority to U.S. Provisional Application No. 61/592,108 filed Jan. 30, 2012, the disclosures of which are hereby incorporated in their entirety by reference.

BACKGROUND OF THE INVENTION

1. Field of the Invention

The present invention relates to compositions for use in medical procedures and methods for use thereof. More specifically, the invention relates to compositions of tissue, including stem cells, useful for regenerating tissue in disease, specifically in penile disease and defects.

2. Description of Related Art

Use of stem cells has grown exponentially over the past two decades as methods of isolating and purifying these cells has become simpler and more cost-effective. In particular, with the advent of the ability to obtain adult stem cells, as opposed to politically-charged embryonic stem cells, work in the field has blossomed. Stem cells have been suggested as a cure for ailments ranging from Parkinson's disease (replacing dying dopaminergic cells of the substantia nigra) to myocardial infarctions and cardiomyopathy. Gimble J M et al. Adipose-derived stem cells for regenerative medicine. *Circulation Res.* 2007; 100: 1249-1260; Kondo K et al. Implantation of adipose-derived regenerative cells enhances ischemia-induced angiogenesis. *Arteriosclerosis, Thrombosis, and Vascular Biol.* 2009; 29: 61-66.

Other defects and diseases may also be candidates for stem cell intervention. One area of interest is that of penile defects, such as erectile dysfunction (ED) and Peyronie's disease. At least some forms of ED trace their etiology to vascular deficits in the penile tissue. Pharmaceutical compositions for treating ED do exist; however, a need exists for a treatment that does not require use of medicaments. At least one group has reported success in the use of stem cells derived from bone marrow to reverse ED in an animal model. Kendirci M et al. Transplantation of non-hematopoietic adult bone marrow stem/progenitor cells isolated by the p75 nerve growth factor receptor into the penis rescues ED in a rat model of cavernous nerve injury. *J. Urol.* 2010; 184(4): 1560-1566. Another group has seen success in using muscle-derived stem cells in a rat model of ED. Woo J C et al. Transplantation of muscle-derived stem cells into the corpus cavernosum restores erectile function in a rat model of cavernous nerve injury. *Korean J. Urol.* 2011; 52: 359-363.

Peyronie's disease is an ailment involving the growth of fibrous plaques in the soft tissue of the penis. These plaques grow in the tunica albuginea, a region of connective tissue that is part of the more general connective tissue of Buck's fascia. The tunica albuginea is an area surrounding the corpora cavernosa. The disease results in pain, ED, and alteration of penis shape, and may be caused by disorganized collagen fibers. Treatments for the disease currently include administration of corticosteroids to the plaques, radiation therapy, and vitamin E. Pharmaceuticals for treatment exist; however, the use of medicaments is considered controversial in the art, and these compounds have not met with sustained success. Hauck E W et al. A critical analysis of nonsurgical treatment of Peyronie's disease. *European Urology* 2006; 49(6): 987-97.

In light of the above, a need exists in the art for a composition of stem cells that is easy to obtain and isolate and a method for use of stem cells in treating penile defects.

SUMMARY OF THE INVENTION

The present invention provides a composition, the composition comprising adipose tissue and at least one isolated stem cell. In non-limiting embodiments, the at least one stem cell is placental or embryonic in origin. In other non-limiting embodiments, the at least one stem cell is a mesenchymal stem cell. In certain non-limiting embodiments, the at least one stem cell is an adipose-derived stem and regenerative cell (ADRC). In further non-limiting embodiments, the stem cell and adipose tissue are derived from a donor. In certain further non-limiting embodiments, the stem cell is an ADRC and it is derived from a donor. In further non-limiting embodiments the at least one stem cell is genetically engineered.

In additional non-limiting embodiments, the composition includes at least one additional additive. The additive may be a compound useful in wound healing, in decreasing inflammation, in breaking down collagen, or in promoting angiogenesis and/or vasculogenesis. In further non-limiting embodiments the composition includes a growth scaffold.

The present invention also provides a method of treating a penile defect in a subject, comprising providing a composition comprising at least one isolated stem cell, and implanting the composition with the penis of the subject. In certain non-limiting embodiments, the composition comprises adipose tissue and stem cells, which may be derived from the subject. In non-limiting embodiments, the at least one stem cell is placental or embryonic in origin. In other non-limiting embodiments, the at least one stem cell is a mesenchymal stem cell. In certain further non-limiting embodiments, the at least one stem cell is an ADRC. In further non-limiting embodiments, the adipose tissue and ADRC are derived from the subject. In non-limiting embodiments, the composition is implanted into the subject's penis. In further non-limiting embodiments, the composition is implanted into or around the subject's corpus cavernosum. In another non-limiting embodiment, the composition is implanted into or around the subject's tunica albuginea. In certain embodiments the composition is injected into the tissue of interest. In other non-limiting embodiments the composition is injected or infused into any artery that feeds penile tissue. In certain non-limiting embodiments, the composition is injected or infused into the corporal arteries or internal pudendal arteries.

In additional embodiments, the composition that is implanted includes at least one additional additive. The additive may be a compound useful in wound healing, in decreasing inflammation, in breaking down collagen, or in promoting angiogenesis and/or vasculogenesis. In further non-limiting embodiments the composition includes an implantable or injectable growth scaffold.

The present invention also provides a method of treating Peyronie's disease by injecting a composition comprising at least one mesenchymal stem cell, at least one component of extracellular matrix, and at least one growth factor, and injecting that composition into the tunica albuginea of a subject in need of treatment for Peyronie's disease.

DESCRIPTION OF THE PREFERRED EMBODIMENTS

The following description is merely exemplary in nature and is in no way intended to limit the invention, its application, or uses.

Provided herein is a composition, the composition compromising adipose tissue and at least one isolated stem cell.

In certain non-limiting embodiments, the at least one stem cell is a mesenchymal stem cell, preferably an adipose-derived stem and regenerative cell (ADRC). In further non-limiting embodiments, the stem cell and adipose tissue are derived from a donor. In certain further non-limiting embodiments, the stem cell is an ADRC and it is derived from a donor. In further non-limiting embodiments the at least one stem cell is genetically engineered.

In certain non-limiting embodiments, the composition includes at least one additional additive. The additive may be a compound useful in wound healing, in decreasing inflammation, in breaking down collagen, or in promoting angiogenesis and/or vasculogenesis. In further non-limiting embodiments the composition includes a growth scaffold.

The present invention also provides a method of treating a penile defect in a subject, comprising providing a composition comprising at least one isolated stem cell, and implanting the composition with the subject.

In certain non-limiting embodiments, the composition includes adipose tissue and stem cells, which may be derived from the subject. In certain further non-limiting embodiments, the at least one stem cell is a mesenchymal stem cell, preferably an adipose-derived stem and regenerative cell (ADRC). In further non-limiting embodiments, the adipose tissue and ADRC are derived from the subject. In non-limiting embodiments, the composition is implanted into the subject's penis. In further non-limiting embodiments, the composition is implanted into or around at least one of the subject's corpus cavernosum. In another non-limiting embodiment, the composition is implanted into or around the subject's tunica albuginea. In other non-limiting embodiments the composition is injected or infused into any artery that feeds penile tissue. In certain non-limiting embodiments, the composition is injected or infused into the corporal arteries or internal pudendal arteries.

In additional embodiments, the composition that is implanted includes at least one additional additive. The additive may be a compound useful in wound healing, in decreasing inflammation, in breaking down collagen, or in promoting angiogenesis and/or vasculogenesis. In further non-limiting embodiments the composition includes an implantable or injectable growth scaffold.

While particular focus is on the use of ADRCs in the composition and method described herein, any type of stem cell, defined below, may be used to advantageously promote vasculogenesis and wound healing in penile defects. These properties function to address defects and diseases such as ED. Additionally, ADRCs may be provided directly to plaques in Peyronie's disease, stimulating wound healing. ADRCs are preferable for stem cell derived treatments of these defects because of their ability to stimulate vasculogenesis and to produce organized collagen. Thomas J. Stem cells repair damaged corneas in mice. Healing Well. Apr. 10, 2009, available at http://news.healingwell.com/index.php?p=news1&id=625948.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines or type of stem cell, constructs, additives, and reagents described herein. It is also to be understood that the terminology used herein is for the purpose of describing particular embodiments only, and is not intended to limit the scope of the present invention which will be limited only by the appended claims.

The term "stem cell" refers to any multipotent or pluripotent cell, traditional stem cells, progenitor cells, prepro-genitor cells, and reserve cells. The term is used interchangeably with and may mean progenitor cell. The stem cell may be derived from an adult organism or from a cell line, or from an embryonic organism. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, and the like. Descriptions of stem cells, including method for isolating and culturing them, may be found in, among other places, Embryonic Stem Cells, Methods and Protocols, Turksen ed., Humana Press, 2002.

The term "adult" as used herein refers to any non-embryonic organism. For example the term "adult adipose-derived regenerative cell," refers to an adipose-derived regenerative cell, other than that obtained from an embryo.

The term "embryo" as used herein refers to any multi-cellular diploid eukaryote during development, until birth or hatching. The term "embryonic stem cell" refers to a pluripotent cell derived from the inner cell mass of a blastocyst.

The term "mesenchymal stem cell" refers to any multi-potent stromal cell derived from, for example and without limitation, umbilical cord blood, adipose tissue, muscle, corneal stroma, and dental pulp that can differentiate into cells such as, including but not limited to, osteoblasts, chondrocytes, and adipocytes.

The term "adipose-derived regenerative cell" (ADRC) is used interchangeably with adipose stem cells (ASC) herein and refers to adult cells that originate from adipose tissue. ADRC are a heterologous population of cells comprising at least one of the following population of cells; adult stem cells, vascular endothelial cells, vascular smooth muscle cells, endothelial cells, mesenchymal stem cells, fibroblasts, pericytes and additional other cell types.

In some embodiments, ADRC refers to a substantially pure population of adipose-derived stem cells. ADRC can be easily harvested from adipose tissue and are substantially free of adipocytes and red blood cells and clonal populations of connective tissue stem cells. The stromal vascular fraction cells are substantially devoid of extracellular matrix material from adipose tissue. ADRC may also be referred to as adipose-derived stem/stromal cells (ASCs), adipose-derived adult stem (ADAS) cells, adipose-derived adult stromal cells, adipose-derived stromal cells, adipose stromal cells, adipose mesenchymal cells, adipose-derived mesenchymal stem cells, lipoblasts, pericytes, preadipocytes, and processed lipoaspirate cells.

The term "adipose" as used herein refers to any fat tissue from a subject. The terms "adipose" and "adipose tissue" are used interchangeably herein. The adipose tissue may be brown fat, white fat or yellow fat or white adipose tissue, derived from subcutaneous, omental/visceral, mammary, gonadal, or other adipose tissue site. The adipose tissue has adipocytes and stroma. Adipose tissue is found throughout the body of an animal. For example, in mammals, adipose tissue is present in the omentum, bone marrow, subcutaneous space, and surrounding most organs. Such cells may comprise a primary cell culture or an immortalized cell line. The adipose tissue may be from any organism having fat tissue.

Preferably, the adipose tissue is human; most preferably, the adipose tissue is derived from the individual in need of treatment for a penile defect. A convenient source of adipose tissue is from liposuction surgery, however, the source of adipose tissue or the method of isolation of adipose tissue is not critical to the invention, and acquisition of adipose tissue by any means may adequately provide tissue and stem cells for the present invention.

The term "tissue" as used herein is a broad term that is applied to any group of cells that perform specific functions, and includes in some instances whole organs and/or part of organs. A tissue need not form a layer, and thus encompasses a wide range of tissue, including adipose tissue derived from any source in an organism. Preferably, the tissue is derived from a mammal. Most preferably, the tissue is derived from the individual in need of treatment for a penile defect.

The term "implant" as used herein refers to any method for transferring a population of cells or cell mass into a subject, including by surgical implantation (incision into the tissue of interest and deposition therein) and injection by a syringe, needle, cannula, or the like of any suitable gauge. An implant as used herein can comprise genetically modified cells, as well as cells differentiated from other cells, such as stem cells, progenitors, and the like, as well as adipose cells or tissue.

The term "corpus cavernosum" of the penis refers to one of a pair of sponge-like regions of erectile tissue which contain most of the blood in the penis during penile erection. Generally, the two corpus cavernosum and a corpus spongiosum are three expandable erectile tissues along the length of the penis which fill with blood during erection. The term "corpus" is used interchangeably herein with corporal, corporeal and corporic, which are terms used to describe tissues which are derived from the corpora cavernosum or which can be developed, differentiated, or altered by natural or artificial means into corpora cavernosum tissue. The term "cavernosum" is used interchangeably herein as cavernae, corporum, cavernosum, or cavernosorum penis, and refers to the caverns of corpora cavernosa (or one of the two corpus cavernosum) of the penis or the dilatable spaces within the corpus cavernosum of the penis, which fill with blood and become distended with erection.

The term "tunica albuginea" refers to the fibrous tissue covering, or enveloping, the corpora cavernosa of the penis. This tissue consists of elastin and collagen. The term "Buck's fascia" refers to the layer of fascia covering the penis, including the tunica albuginea.

The terms "subject" and "individual" are used interchangeably herein, and refer to an animal, for example a human, from whom a adipose tissue and stem cells, for example ADRC can be harvested, or a subject into whom tissue can be transplanted for treatment, for example treatment for penile defects, using the compositions and methods described herein. For treatment of conditions or disease states which are specific for a specific animal such as a human subject, the term "subject" refers to that specific animal. In some embodiments, the subject is a human subject. It is possible in embodiments of this invention that recipient subjects are of a different mammalian subject than the donor subject.

Compositions and Methods for Treatment of Penile Defects, Peyronie's Disease, Erectile Dysfunction One aspect of the present invention provides for a composition. The composition comprises adipose tissue and at least one isolated stem cell. The composition is one that is suitable for implantation into a subject, for example an animal, preferably a mammal. In a preferred non-limiting embodiment, the composition is suitable for implantation into a human. In a further preferred non-limiting embodiment, the adipose tissue and at least one stem cell of the composition are suitable for implantation into a human because they are derived from the same human subject.

The at least one stem cell may be any type of stem cell, including but not limited to mesenchymal stem cells. The stem cells may be obtained from any suitable source, for example, and without limitation, stem cells may be obtained from adult or embryonic sources, from bone marrow, from placental tissue, from umbilical cord blood, and from adipose tissue. In preferred, non-limiting embodiments, the stem cell is obtained from adipose tissue, and is an adipose-derived regenerative cell (ADRC).

In general, adipose tissue may be collected in any suitable manner. For example, in non-limiting embodiments, adipose tissue is obtained through dry liposuction, wet liposuction, super-wet liposuction, tumescent liposuction, power-assisted liposuction, laser-assisted liposuction, or the like.

Once harvested by any suitable method, adipose tissue may be processed by any known method. The following methods are to be considered exemplary, and non-limiting. In a preferred, non-limiting embodiment, adipose tissue is processed using the StemSource® Cellbank or Cytori Celution® System. The Cytori procedure and system therefore are disclosed in detail in U.S. Pat. Nos. 7,501,115 and 7,687,059. Briefly, adipose tissue is harvested from a subject. In a preferred, non-limiting embodiment of the current invention, the subject is an individual in need of treatment for a penile defect. The tissue is processed to remove mature adipocytes and connective tissue from the sample. Processing may occur within a system having a tissue collection port, filter disposed within the system, and a mixing container for holding the processed sample. The filter works to remove the unwanted cells and non-cellular materials from the sample, enriching the proportion of ADRCs in the filtered sample.

The Cytori system has successfully been used in providing ADRCs for breast tissue implantation for reconstruction after radical lumpectomy, proving the ability of stem cells isolated by this method to generate tissue of a single type (adipocytes, or fat). Similarly, in treatment of penile defects, only one type of tissue need be generated. As such, the Cytori method and system is optimal for use in preparing the composition of the current invention.

With regard to use of the Cytori system and method itself, processing is accomplished by washing and disaggregating the tissue to reduce the presence of free lipids and blood elements. Processing may or may not also include a rinsing step; the step conducted using isotonic saline or any other suitable physiologic solution known to those skilled in the art.

Remaining tissue is then disaggregated using enzyme degradation or mechanical disaggregation. The cells and solution are then centrifuged to separate cells, including ADRC, from the degradation solution. The cells form a pellet in the centrifuge, and the pellet can be frozen for storage or resuspended in another solution, for example a buffer, for use in medical treatments such as those recited herein.

The concentration of stem cells obtained by this method may vary, but typically approximately 0.1% of the cells in the pellet are stem cells. Greater percentages may be obtained by varying the above method, for example by use of adherence protocols such as described in Berdel W E et al., Purification of human monocytes by adherence to polymeric fluorocarbon. *Immunobiology* 1982 163(5): 511-520, or by separation on the basis of cell-surface markers, for example on the basis of markers present on differentiated cells, such as CD34 and the like, or by selecting based on markers expressed on progenitor cells, such as CD90 and the like. In a preferred, non-limiting embodiment, the percentage of stem cells present in the pellet is between approximately 2% and 12%.

For embodiments where the individual to be treated is not the donor of the adipose tissue and at least one stem cell, the composition may further comprise immunosuppressive agents designed to prevent rejection of the composition once implanted. Immunosuppressive agents may be selected from glucocorticoids, cytostatics, antibodies, pharmaceuticals such as tacrolimus, ciclosporin, sirolimus, interferons, opioids, mycophenolic acid, fingolimod, and myriocin.

In other non-limiting embodiments adipose tissue is derived from lipoaspirate (i.e. from liposuction), is washed, exposed to a collagenase digest at 37 degrees Celsius, and centrifuged.

In a non-limiting embodiment, ADRCs are isolated from adipose tissue by triplicate washing in 01 mol/L phosphate-buffered saline (PBS), pH=7.4. Tissue is then minced and digested in 0.1% collagenase type I at 37 degrees Celsius for 45 minutes. Afterwards, the solution is filtered and centrifuged at 800 g for eight minutes. Supernatant is removed and cells are resuspended in Modified Eagle's Medium (MEM) supplemented with 10% fetal bovine serum (FBS). Cells are then plated and incubated at 37 degrees Celsius.

ADRCs are harvested from the growth by flow cytometry according to traditional flow cytometry methods, for example as disclosed in Alexander C M et al. Separating stem cells by flow cytometry: reducing variability for solid tissues. *Cell Stem Cell* 2009; 5: 579-83 and Online Supplemental Material. Cells are washed in buffer (FBS) and incubated for 30 minutes in FBS with antibodies against CD105, CD90, CD34, and/or CD45. The ADRCs are then combined with adipose cells in a composition for injection.

In non-limiting embodiments, the ADRCs are processed by washing in PBS followed by ECM digestion in 0.075% collagenase for 30 minutes at 37 degrees Celsius. Digestion is neutralized using Dulbecco's Modified Eagle Medium (DMEM) containing 10% FBS. Digested tissue is then centrifuged at 1200 g for 10 minutes to obtain a cell pellet. The pellet is then resuspended and filtered, and cells are plated. Cell media is removed 12-18 hours later and fresh media provided. Cells are incubated on ice with antibodies to human CD11b, CD18, CD31, CD34, CD38, CD44, CD45, CD54, CD62L, CD90, CD105, CD106, CD117, CD133, CD144, CD166, and/or CD271. Cells are then washed and flow cytometry, for example fluorescence-activated cell sorting, is performed according to traditional, known methods, for example as disclosed in Alexander C M et al. Separating stem cells by flow cytometry: reducing variability for solid tissues. *Cell Stem Cell* 2009; 5: 579-83 and Online Supplemental Material.

While specific ADRC isolation procedures are provided herein, the invention described should not be limited to those procedures. It should be apparent to those skilled in the art that other means of isolating stem cells, in particular ADRC cells, are possible and may be used interchangeably with the current invention.

While the process for obtaining adipose tissue and ASCs is described in detail and is a preferred, non-limiting embodiment, other sources of stem cells are within the scope and spirit of the present invention.

In non-limiting embodiments, the stem cell used in the present composition is a mesenchymal stem cell isolated from bone marrow. In certain preferred non-limiting embodiments, the bone marrow is that of the patient in need of treatment for a penile defect. Such stem cells may be isolated in accordance with the following protocol, which is to be considered exemplary and non-limiting.

Bone marrow tissue may be obtained from the head of the femur, by transversally segmenting the femoral head to expose trabecular, or cancellous, bone. This trabecular bone may be extracted with successive, serial washes of phosphate-buffered saline (PBS). The solution of PBS and trabecular bone may then be filtered through a filter of any suitable pore diameter, for example and without limitation a 40, 70, or 100 μm cell strainer. The solution may then be centrifuged at 400 g for 10 minutes to form a pellet of cells, the supernatant aspirated, and the pellet resuspended in media containing DMEM supplemented with 10% FBS and 1% streptomycin or penicillin, or both. Cells may then be cultured, and then washed with PBS to remove non-adherent cells. The obtained cells may be further expanded by repeating the incubation and washing steps until a suitable volume of cells is obtained. Medium may be supplemented with heparin and growth factors, if necessary.

In other non-limiting embodiments, the stem cells may be obtained from placental tissue. Stem cells from this source may be obtained by any method known to those of skill in the art. In certain non-limiting embodiments, stem cells may be obtained according to the following procedure. Tissue samples from placental tissue may be washed in PBS plus antibiotic solution (200 U/mL penicillin and/or 200 mg/mL streptomycin). The amnion is separated from chorion through fine dissection. Small pieces of both membranes are minced and subjected to enzymatic digestion to obtain a mesenchymal population of cells. The resulting cells are seeded in 25 cm$^2$ culture flasks with 5 mL of DMEM with 20% FBS and antibiotics (penicillin 100 U/mL and/or streptomycin 100 mg/mL), and incubated at 37 degrees Celsius. Nonadherent cells are removed with changes of medium (DMEM plus 10% FBS). The obtained cells may be further expanded by repeating the incubation and washing steps until a suitable volume of cells is obtained. Medium may be supplemented with heparin and growth factors, if necessary.

In addition to the protocols described herein, stem cells may be obtained from any suitable commercial source for use in the composition of the present invention. In non-limiting embodiments, mesenchymal stem cells from placental tissue provided under the trade name Ovation® by Osiris Therapeutics, Inc. may be used. This product is preferred because it includes components of extracellular matrix (ECM) and growth factors.

In certain non-limiting embodiments, the composition further comprises other agents. These agents may include compositions designed to assist in reducing inflammation, aiding wound healing, promoting angiogenesis and/or vasculogenesis, and degrading collagen. Agents useful for reducing inflammation include, but are not limited to, anti-inflammatory cytokines such as interleukin-4 (IL-4), IL-6, IL-10, IL-11, and IL-13. Cytokines are cell-signaling molecules, which may be categorized as peptides, proteins, or glycoproteins. IL-1 receptor antagonists (IL-1Ra) may also be included in the composition to reduce inflammation in the area of treatment. In certain non-limiting embodiments, the anti-inflammatory agents may include free radical scavengers or antioxidants such as, without limitation, glutathione, selenium, vitamin E, vitamin C, and/or beta-carotene.

Agents useful for enhancing wound healing that may be included with the composition of the present invention include, but are not limited to, growth factors, collagenases, fullerenes and derivatives thereof, pseudopterosin-based compounds, histatin, anti-fibrotic compounds such as tumor growth factor-beta inhibitors, analgesics, and the like. In preferred, non-limiting embodiments, the agent useful for wound healing is fibroblast growth factor (FGF).

Agents useful for enhancing angiogenesis and/or vasculogenesis that may be included with the composition of the present invention include, but are not limited to, growth factors, matrix mealloproteinases (MMPs), and angiopoietins (Ang1 and Ang2). The growth factors useful in the present composition include the vascular endothelial growth factor (VEGF) family including VEGF-A, VEGF-B, VEGF-C, VEGF-D, and placental growth factor (PGF), and the FGF family (FGF-1 and FGF-2). In certain preferred non-limiting embodiments, the agent useful for enhancing angiogenesis and/or vasculogenesis is selected from the VEGF family.

As Peyronie's disease is known to result from disorganized collagen, in certain preferred embodiments it is also useful to include a collagenase in the composition, to aid in the breaking down of disorganized collagen in the plaques associated with the disease. Collagenases are enzymes that break the peptide bonds in collagen and aid in breaking down the protein. Collagenases useful in the composition of the present invention may include MMPs and collagenase clostridial histolyticum (available from Auxilium Pharmaceuticals under the trade name Xiaflex®).

The composition of the present invention may further include a biologic matrix or growth scaffold on which the adipose tissue and stem cells are present. In some embodiments the matrix is a degradable matrix, such that after implantation, the matrix is slowly dissolved by the body's natural processes. Such a scaffold may include collagen fibers or bundles, for example the Three Dimensional Collagen Composite Scaffold available from Becton, Dickinson and Company. Other scaffolds may be formed from isolated components of ECM, or whole ECM. Such scaffolds are available, for example, from Kensey Nash under the trade name Meso BioMatrix™ and include porcine mesothelial ECM.

In addition, scaffolds made from synthetic materials may also be used in the composition of the present invention. These scaffolds may be provided by any known process familiar to those in the polymer arts. The synthetic scaffold may include a fabric that can be attached to the site of interest by sutures or the like, or a may be held in place by an adhesive that is acceptable for use in humans. Such scaffolds can be formed into any suitable shape.

In a preferred, non-limiting embodiment, the composition is provided on an ECM scaffold. The ECM may be obtained from any commercial source. The ECM scaffold may be biodegradable or not, but preferably is biodegradable. In such a non-limiting embodiment, the adipose tissue and at least one isolated stem cell may be disposed on the surface of the scaffold, or may be embedded within a three-dimensional scaffold. Formation of such scaffolds, through dissociation of tissue, digestion, lyophilization, and reconstitution, may be accomplished by any procedure known to those of skill in the art.

In some non-limiting embodiments, the scaffold is a fibrin scaffold that is injectable, for example through the method also provided herein. Injectable fibrin scaffolds are known in the art, for example, a group has seen growth of cardiac cells following implantation of ADRCs on a fibrin scaffold via injection. Zhang et al., Preservation of the cardiac function in infracted rat hearts by the transplantation of adipose-derived stem cells with injectable fibrin scaffolds. *Exper. Biol. & Med.* 2010; 235: 1505-1515.

Another aspect of the current invention provides for a method of treating an individual having a penile defect. The method comprises providing a composition of at least one isolated stem cell, and implanting the composition within the penis of the individual. The method may be used for treatment of erectile dysfunction (ED) and Peyronie's disease, among other defects or disorders.

In a non-limiting embodiment, the implanting step comprises providing a biological scaffold or matrix comprising the composition. Examples of suitable biological scaffolds are known to those skilled in the art. In some embodiments the matrix is a degradable matrix, such that after implantation, the matrix is slowly dissolved by the body's natural processes.

In a further preferred embodiment, the composition is provided on an ECM scaffold, for example, from Kensey Nash under the trade name Meso BioMatrix™, and that scaffolding is then implanted into the subject. The ECM scaffold may be biodegradable or not.

In yet another non-limiting embodiment, the composition is implanted into a subject by injection. The pellet of cells obtained by the method provided herein is resuspended in a suitable solution and injected into appropriate areas of the body.

In preferred, non-limiting embodiments, the implantation is directed toward the subject's penis. Implantation into the penis may be at any suitable location or anatomy for addressing the particular defect. Implantation may be of the composition, including in some embodiments adipose tissue and/or a scaffold or matrix, by injection of a solution, or by any other method known for introducing stem cells to a target. In non-limiting embodiments, injection occurs at the target site and is in at least 50 microliter volumes delivered in a needle of suitable gauge for the anatomy.

In further preferred, non-limiting embodiments, the implantation is directed towards at least one of the subject's corpora cavernosa. In preferred, non-limiting embodiments, a solution comprising the composition of isolated stem cells is injected directly into or around at least one of the corpora cavernosa. In preferred, non-limiting embodiments, a solution comprising the composition of isolated stem cells is injected directly into scar tissue present on the penis of an individual with Peyronie's disease. In additional non-limiting embodiments, the composition is injected or infused into any artery that feeds penile tissue. In certain non-limiting embodiments, the composition is injected or infused into the corporal arteries or internal pudendal arteries.

In another non-limiting embodiment, the composition is implanted into or around the subject's tunica albuginea. Stem cells, such as ADRCs in a non-limiting embodiment, stimulate the growth of human tissues. Wounded tissue is most often replaced by scar tissue, such as that present in Peyronie's disease. This scar tissue is characterized in the skin by disorganized collagen structure and irregular vascular structure. Stem cells reorganize collagen and induce vasculogenesis, aiding in wound healing, such as in wounds present in Peyronie's disease. See Thomas J. Stem cells repair damaged corneas in mice. Healing Well. Apr. 10, 2009, available at http://news.healingwell.com/index.php?p=news1&id=625948.

Proliferation and/or differentiation of cells may be accomplished before or after transplantation, and in various combinations of in vitro or in vivo conditions, including (1) proliferation and differentiation in vitro, then transplantation, (2) proliferation in vitro, transplantation, then further proliferation and differentiation in vivo, and (3) proliferation in vitro, transplantation and differentiation in vivo. Those skilled in the art can follow standard methodology to transform the stem cells of the current invention into a desired cell type or engineered construct for use in implantation for the purposes described herein.

EXAMPLES

Example 1

Treatment of Peyronie's Disease

The composition of the present invention is administered to a population having Peyronie's disease. Peyronie's disease is an ailment involving the growth of fibrous scar tissue, or plaques, in the soft tissue of the penis, which results in abnormal bending of the organ. The etiology of the plaques is not known. These plaques grow in the tunica albuginea, a region of connective tissue that is part of the more general connective tissue of Buck's fascia. The tunica albuginea is an area surrounding the corpora cavernosa. The disease results in pain, ED, and alteration of penis shape, and may be caused by disorganized collagen fibers. Treatments for the disease currently include administration of corticosteroids to the plaques, radiation therapy, and vitamin E. Pharmaceuticals for treatment exist; however, the use of medicaments is considered controversial.

Prior to administration of the composition of the present invention, baseline measurements are taken to assess the state of health of the subjects. These assessments include the following:

Subjects will have peak penile artery velocity in the corporal arteries measured with penile doppler and ultrasound. Penile doppler is a standard tool for the evaluation of ED, and is less invasive than typical means for measuring artery velocity, angiography with selective internal iliac angiography. Penile Doppler may be performed with a high frequency transducer (7.5-9.0 MHz), and at least the inner diameter of the cavernosal artery, baseline peak systolic velocity, and end diastolic velocity are measured. A normal value for inner diameter of the cavernosal artery is 0.3-0.5 mm. In a flaccid state, monophasic flow should be seen in an individual without Peyronie's disease. In an erect state, a velocity of greater than 30 cm/sec should be observed in an individual without ED, which is often a symptom of Peyronie's disease.

In addition to penile artery velocity, the size of fibrous plaques present on the penis are also assessed prior to the initiation of any treatment. This may be done with ultrasound, at which time the grade of Peyronie's may be assigned to the subject. Peyronie's grades are given according to the following: Grade 1 (plaque less than 0.3 cm), Grade 2 (greater than 0.3 cm and less than 1.5 cm), and Grade 3 (greater than 1.5 cm, or two plaques greater than 1 cm).

Angle of penile curvature, a hallmark of Peyronie's disease, is also measured prior to initiation of any treatment. Curvature may be assigned a grade according to the following, based on the Kelami classification system: Grade 1 (curvature of 30 degrees or less), Grade 2 (curvature of 30 degrees to 60 degrees), and Grade 3 (curvature of greater than 60 degrees).

A penile rigidity test is also performed prior to any initiation of treatment. This test may be done as a nocturnal penile tumescence (NPT test) or an intracavernosal injection test. In an NPT test, the frequency and quality of an erection during sleep is assessed by either placing a ring-like device around the subject's penis, or by use of an electronic monitoring device. The ring-like device is a simple mechanical device consisting of plastic films, which shear at certain pressures, for example when an erection provides sufficient pressure on the ring to break the film. The electronic measurement includes a device that measures frequency, temporal length, and rigidity of erections during sleep. This is a preferred means for measuring rigidity. These variations of the NPT test may be conducted in a polysomnography or other sleep lab, or at the subject's home. The NPT test is usually performed over two consecutive nights for accuracy.

Another form of the rigidity test, the intracavernosal injection test, involves injection of alprostadil (a formulation of prostaglandin $E_1$ available under the trade names Edex® from actient pharmaceuticals and Caverject® from Pfizer) or Tri-Mix (a mixture of Prostaglandin $E_1$, Phentolamine, and Papaverine) into the base of the penis, which causes an erection through its vasodilator properties. Following the injection, fullness and length of the erection are measured. The test may be repeated as necessary for increased accuracy. The length and circumference of each subject's penis is also assessed prior to treatment.

Subjects are also given the International Index of Erectile Function (IIEF) Questionnaire prior to any initiation of treatment. This questionnaire asks subjects to rate various parameters relating to ED by answering fifteen questions, and assigns point values from zero to five to each answer. A score of 25-30 indicates no ED, and a score of 0-6 indicates severe ED. A continuum of moderate to mild ED exists between a score of 7 and 24. A shortened version of the IIEF, the IIEF-5 may be administered. In this short form, five questions are to be answered, and a score of 22-25 means that the subject does not have ED, and a score of 5-7 means the subject has severe ED. A continuum of moderate to mild ED exists between a score of 7 and 22.

Following baseline measurements of the above variables, the composition including adipose tissue and stem cells is administered to the subject by implantation in the penis. This implantation is by surgical incision and implantation with a biodegradable scaffold having adipose tissue and stem cells present therein, by injection of the composition on an injectable fibrin scaffold, or injection of adipose tissue and stem cell alone, or with an injectable fibrin scaffold. Various groups including other elements such as growth factors, anti-inflammatories, antioxidants, and collagenases are included. Injections are made into the tunica albuginea surrounding the corpora cavernosa and/or the corpora cavernosa themselves, any artery feeding penile tissue, or the corporal arteries or internal pudendal arteries. Repeated injections may be necessary.

Following administration of the composition, follow-up observations, including each of the aforementioned variables (arterial velocity, penile plaque size, penile curvature, IIEF score, and rigidity testing) are collected at three months, six months, and twelve months. Increased velocity, decreased plaque size, decreased curvature, increased IIEF score, and increased rigidity are expected. Shortening of time for improvement is expected in those receiving collagenase as well.

Example 2

Treatment of Erectile Dysfunction

The composition of the present invention is administered to a population having ED. ED is an ailment in which a male is unable to achieve or sustain an erection suitable for sexual intercourse. A number of factors are believed to play a role in or be directly responsible for ED, including obesity, blood pressure, chronic illnesses such as diabetes, poor blood flow to the penis, smoking tobacco, alcoholism, and side-effects of other medications.

Treatments for ED currently include cessation of potential causes such as smoking tobacco and consumption of alcohol, hormone (testosterone) replacement, surgery, and administration of pharmaceuticals such as vardenafil, tadalafil, and sildenafil. Some of these pharmaceuticals are controversial for their incompatibility with nitrate drugs, and for their unwanted side-effects, such as effects on vision (blurring, loss of vision) and priapism.

Prior to administration of the composition of the present invention, baseline measurements are taken to assess the state of health of the subjects. These assessments include the following:

Subjects will have peak penile artery velocity in the corporal arteries measured with penile doppler and ultrasound. Penile doppler is a standard tool for the evaluation of ED, and is less invasive than typical means for measuring artery velocity, angiography with selective internal iliac angiography. Penile Doppler may be performed with a high frequency transducer (7.5-9.0 MHz), and at least the inner diameter of the cavernosal artery, baseline peak systolic velocity, and end diastolic velocity are measured. A normal value for inner diameter of the cavernosal artery is 0.3-0.5 mm. In a flaccid state, monophasic flow should be seen. In an erect state, a velocity of greater than 30 cm/sec should be observed in an individual without ED.

A penile rigidity test is also performed prior to any initiation of treatment. This test may be done as a nocturnal penile tumescence (NPT test) or an intracavernosal injection test. In an NPT test, the frequency and quality of an erection during sleep is assessed by either placing a ring-like device around the subject's penis, or by use of an electronic monitoring device. The ring-like device is a simple mechanical device consisting of plastic films, which shear at certain pressures, for example when an erection provides sufficient pressure on the ring to break the film. The electronic measurement includes a device that measures frequency, temporal length, and rigidity of erections during sleep. This is a preferred means for measuring rigidity. These variations of the NPT test may be conducted in a polysomnography or other sleep lab, or at the subject's home. The NPT test is usually performed over two consecutive nights for accuracy.

Another form of the rigidity test, the intracavernosal injection test, involves injection of alprostadil (a formulation of prostaglandin $E_1$ available under the trade names Edex® from actient pharmaceuticals and Caverject® from Pfizer) or Tri-Mix (a mixture of Prostaglandin $E_1$, Phentolamine, and Papaverine) into the base of the penis, which causes an erection through its vasodilator properties. Following the injection, fullness and length of the erection are measured. The test may be repeated as necessary for increased accuracy. The length and circumference of each subject's penis is also assessed prior to treatment.

Subjects are also given the International Index of Erectile Function (IIEF) Questionnaire prior to any initiation of treatment. This questionnaire asks subjects to rate various parameters relating to ED by answering fifteen questions, and assigns point values from zero to five to each answer. A score of 25-30 indicates no ED, and a score of 0-6 indicates severe ED. A continuum of moderate to mild ED exists between a score of 7 and 24. A shortened version of the IIEF, the IIEF-5 may be administered. In this short form, five questions are to be answered, and a score of 22-25 means that the subject does not have ED, and a score of 5-7 means the subject has severe ED. A continuum of moderate to mild ED exists between a score of 7 and 22.

Following baseline measurements of the above variables, the composition including adipose tissue and stem cells is administered to the subject by implantation in the penis. This implantation is by surgical incision and implantation with a biodegradable scaffold having adipose tissue and stem cells present therein, by injection of the composition on an injectable fibrin scaffold, or injection of adipose tissue and stem cell alone. Various groups including other elements such as growth factors, anti-inflammatories, antioxidants, and collagenases are included. Injections are made into the tunica albuginea surrounding the corpora cavernosa and/or the corpora cavernosa themselves, any artery feeding penile tissue, or the corporal arteries or internal pudendal arteries. Repeated injections may be necessary.

Following administration of the composition, follow-up observations, including each of the aforementioned variables (arterial velocity, rigidity testing, and IIEF score) are collected at three months, six months, and twelve months. Increased velocity, increased IIEF score, and increased rigidity are expected.

While the present invention has been described in connection with the preferred embodiments, it is to be understood that other similar embodiments may be used or modifications and additions may be made to the described embodiments for performing the same function of the present invention without deviating therefrom. Therefore, the present invention should not be limited to any single embodiment, but rather construed in breadth and scope in accordance with the recitation of the appended claims.

The invention claimed is:

1. A method of treating a human subject with a penile defect comprising the steps of:
providing a composition comprising at least one isolated stem cell, at least one component of extracellular matrix, and at least one growth factor and resuspending in a suitable solution for injection; and
implanting the composition within the penis of a human subject in need of treatment for a penile defect exhibiting erectile dysfunction or Peyronie's disease exhibiting disorganized collagen, plaque or fibrosis scar tissue wherein the composition is implanted into or around at least one of the subject's corpora cavernosa or within the tunica albuginea surrounding the at least one corpora cavernosa, wherein the implanting step comprises injecting at least 50 microliter volumes of the composition suspended in the solution into the subject;

wherein the at least one component of extracellular matrix comprises collagen and collagenase, the collagenase being collagenase clostridial *histolyticum* and wherein the at least one isolated stem cell is a placental stem cell, and wherein the collagenase breaks down disorganized collagen in the plaque associated with disease while introducing collagen.

2. The method according to claim 1, wherein the at least one isolated stem cell is a mesenchymal stem cell.

3. The method of claim 1, wherein the defect is erectile dysfunction.

4. The method of claim 1, wherein the composition comprises at least one additional agent.

5. The method of claim 4, wherein the at least one additional agent promotes at least one of wound healing, angiogenesis, vasculogenesis, and degradation of collagen.

6. The method of claim 4, wherein the at least one additional agent is an anti-inflammatory or an antioxidant.

7. A method of treating a human subject with a penile defect comprising the steps of:

providing a composition comprising at least one isolated stem cell, at least one component of extracellular matrix, and at least one growth factor and resuspending in a suitable solution for injection, wherein the composition comprises at least one additional agent, wherein the at least one additional agent promotes at least one of wound healing, angiogenesis, vasculogenesis, and degradation of collagen, wherein the at least one additional agent is an anti-inflammatory or an antioxidant; and implanting the composition within the penis of a human subject in need of treatment for a penile defect wherein the composition is implanted into or around at least one of the subject's corpora cavernosa or within the tunica albuginea surrounding the at least one corpora cavernosa, wherein the implanting step comprises injecting at least 50 microliter volumes of the composition suspended in the solution into the subject;

wherein the at least one component of extracellular matrix comprises collagen and collagenase, the collagenase being collagenase clostridial *histolyticum* and wherein the at least one isolated stem cell is a placental stem cell, and wherein the collagenase breaks down collagen while introducing collagen.

* * * * *